(12) United States Patent
Dungworth et al.

(10) Patent No.: US 6,329,057 B1
(45) Date of Patent: *Dec. 11, 2001

(54) PARTICLES HAVING SURFACE PROPERTIES AND METHODS OF MAKING THEM

(75) Inventors: Howard Roger Dungworth, Halifax; Bryan David Grey, Bradford; John Robert Stockwell, Skipton, all of (GB)

(73) Assignee: CIBA Specialty Chemicals Water Treatments Limited, Bradford (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/997,090

(22) Filed: Dec. 23, 1997

(30) Foreign Application Priority Data

Dec. 23, 1996 (EP) .................................................. 96309466

(51) Int. Cl.$^7$ ........................................................ B32B 5/16
(52) U.S. Cl. ........................... 428/403; 428/407; 523/201; 523/202
(58) Field of Search ................................... 428/403, 407; 523/201, 202

(56) References Cited

U.S. PATENT DOCUMENTS

| | | | |
|---|---|---|---|
| 3,975,280 | * | 8/1976 | Hachmann et al. ................. 252/102 |
| 4,003,841 | * | 1/1977 | Hachmann et al. .................... 252/94 |
| 4,497,718 | * | 2/1985 | Neiditch et al. ..................... 252/8.75 |
| 4,777,089 | * | 10/1988 | Takizawa et al. ................ 428/402.22 |
| 4,842,761 | * | 6/1989 | Rutherford ............................. 252/90 |
| 4,898,781 | * | 2/1990 | Onouchi et al. ................. 428/402.22 |
| 5,281,355 | * | 1/1994 | Tsaur et al. ...................... 252/174.13 |
| 5,385,959 | * | 1/1995 | Tsaur et al. ........................... 523/201 |

FOREIGN PATENT DOCUMENTS

| | | |
|---|---|---|
| 0 285 694 | 10/1988 | (EP) . |
| 0 297 605 | 1/1989 | (EP) . |
| 90/08478 | 8/1990 | (WO) . |

* cited by examiner

*Primary Examiner*—H. Thi Le
(74) *Attorney, Agent, or Firm*—David R. Crichton

(57) ABSTRACT

Polymer particles comprising a hydrophobic organic matrix and located at the exterior free cationic groups and a further polymer which comprises free hydroxy groups. The particles are produced by an aqueous suspension polymerization process wherein the continuous aqueous phase contains a polymerization stabilizer and a dissolved vinyl addition cationic monomer. The polymerization stabilizer can be any suitable polymer that comprises free hydroxy groups. The process results in polymers of average particle size in the range 50 to 150 microns and reduced levels of undesired polymer emulsion or undersized particles. The particles are particularly useful for absorbing water insoluble active ingredients, such as insecticides, insect repellents, fragrances, pheromones for subsequent slow release. The cationic surface character of said polymer particles makes them especially useful for forming stable dispersions or slurries in active concentrates such as perfume bases or detergent concentrates. Furthermore these dispersions or slurries remain stable and substantially free of agglomerates. The particles containing active ingredient readily associate with fabrics such as cotton, wool and viscose where the active ingredient is released in a controlled fashion over several days.

20 Claims, No Drawings

PARTICLES HAVING SURFACE PROPERTIES AND METHODS OF MAKING THEM

This invention relates to particles having surface properties and methods of making them.

It is concerned to provide surface properties on the particles that will cause them to be more firmly retained on substrates such as fabrics, vitreous surfaces or the skin. In the invention this is achieved by providing a polymer core to the particle with a surface of a different polymer.

These particles are particularly suitable for forming a stable-dispersion in a liquid concentrate containing active ingredient, such as a liquid detergent concentrate or liquid rinse conditioner containing a fragrance, wherein the active ingredient becomes imbibed or entrapped within the matrix of the polymer and this provides a product which is suitable for the controlled release of active ingredients.

SUMMARY OF THE PRIOR ART

Various polymer systems have been proposed as diluting systems for active ingredients. WO-A-90/08478 relates to food flavouring high note enhancement by micro-bead impregnated with flavoring containing volatiles and is protected by a soluble or swellable coating. This patent describes porous polymeric beads made from copolymers of divinylbenzene with styrene. The polymeric beads are preferably produced with a coating that retards the release of the flavouring. Illustrative coatings are hydroxyl propyl methyl cellulose and polyvinyl alcohol.

EP-A-297605 is directed to cell culture micro-carriers comprising (meth)acrylic ester polymer particles having positively charged groups on the surface. The polymer particles have an average diameter of between 100 and 1000 microns and are prepared by oil in water type suspension polymerisation of (meth) acrylic ester as a monomer followed by treating the resulting polymer particles with ammonia or amine having 5 or less carbon atoms. Typically polyvinyl alcohol may be used as a stabiliser in the aqueous phase of the polymer. The positive groups are generated by reacting the formed polymer particles with the amine or ammonia. In order for this to be possible it is necessary that the matrix monomer contains functional groups that react with the ammonia or amino compounds, e.g. glycydyl methacrylate.

JP-A-62289238 describes resistant anion exchangers. This patent describes an anionic exchange resin produced by polymerising glycydyl esters with other vinyl compounds and then reacting the polymer particles with ammonia or amines.

WO-A-92/18222 describes the preparation and use of solid non-porous crosslinked polymer beads. The beads are produced by first forming a monomer phase which comprises at least one monoethylenically unsaturated monomer and a monomer soluble initiator. The monomer phase is then combined with an aqueous liquid-phase which is substantially immiscible with the monomer phase to form a reaction mixture. An organic polymer colloid suspending agent can also be combined with the aqueous phase. Preferred suspending agents include polyvinyl polyols having a molecular weight of at least 40,000 and includes polyvinyl alcohol.

U.S. Pat. No. 4,842,761 discloses composite particles comprising a water soluble polymer and a water insoluble polymer. Discrete entities of one polymer are embedded within a matrix of the other polymer. The composite particles are used as perfume carriers in laundry detergents and provide controlled release perfume.

GB-A-2234901 describes a method of encapsulating a water insoluble substance, such as an insecticide, within a carrier capsule. The water insoluble substance is dissolved in a substance which is capable of modifying the carrier capsule so that it imbibes said substance and then entrapping said substance within the thereby modified carrier capsule by removal of the carrier capsule modifying agent. The patent exemplifies starch granules and cellulosic fibres as carrier capsule.

EP-A-285694 is one of a series of documents concerned with porous cross linked polymers obtained by polymerisation around droplets of a liquid substance which may subsequently be removed. These porous polymers can act as carriers for a variety of liquids. They are used in products for application to the skin, and give controlled release of the liquid to the skin.

THE INVENTION

We have now found that the properties of polymer particles—which are insoluble in water—for controlled retention and/or release systems can be improved by providing at the surface of the insoluble particles which are preferably formed from a (meth) acrylic monomer with at least three carbon atoms in the esterifying alcohol, a further polymer with free hydroxyl groups. Such polymer enhances deposition of the particles on substrates. The use of such particles can enhance deposition of perfume or other active ingredients.

The present invention may also provide particles containing an organic polymer core, which are insoluble in water, characterized in that the particles have at their exterior, a different polymer or polymers which provide(s) hydroxy functionality and cationic functionality. There may be a single such different polymer providing both those functionalities.

The cationic functionality may be provided by pendant cationic groups that have been derived from cationic vinyl addition monomer units bonded to the organic water insoluble polymer or cationic monomer units present in the further free hydroxy containing polymer.

The present invention also provides organic polymer particles of average particle size at least 40 microns, which have been produced by a process of suspension polymerization of organic water insoluble vinyl addition monomers in an aqueous medium comprising a hydroxy containing polymeric polymerization stabilizer that has free hydroxy groups, characterised in that a cationic monomer containing a $C_4$–$C_8$ alkyl, aryl, alkaryl or aralkyl pendant groups are also present in the aqueous medium and this cationic monomer becomes incorporated onto the exterior of the polymer particles during the polymerization process.

The polymer particles of this invention are particularly suitable as carriers of active substances, especially those used in controlled release systems. The polymer particles can be dispersed into a liquid concentrate, such as a detergent concentrate or rinse conditioner containing an active ingredient such as a fragrance, so that the active ingredient is imbibed by the polymer particles and becomes entrapped within the polymer matrix. It is important that the particles remain in suspension in the active concentrate and do not agglomerate. The surface cationic character of the particles help stabilize the particles from agglomeration in the active concentrate, especially when such a liquid is an aqueous concentrated fabric conditioning agent.

Surprisingly it has been found that the presence of the functionalities at the exterior of the particles enhances the deposition of the particles onto certain substrates such as fabrics, skin etc. and thereby enhances the delivery of the active ingredient in a controlled fashion. An example of this could be a fabric treatment formulation that contains said particles, in which the active ingredient is an insecticide or insect repellant. The particles have a strong affinity for the fabric due to the hydroxy groups and possibly also by the cationic groups present at the exterior of the polymer particles. The polymer particles release insecticide for a prolonged period thereby preventing the damage to the fabric by insect grubs. The polymer particles also have the advantage of being easily removed from the substrate if required by normal laundering.

The hydrophobic monomer or monomer blend comprises a monoolefinic monomer such as (meth) acrylic esters optionally with other monomers such as styrene and optionally a polyolefinic monomer capable of crosslinking the hydrophobic monomer. In one preferred embodiment the hydrophobic monomer mixture comprises isobutyl methacrylate with 2 mole % divinyl benzene.

The cationic vinyl addition monomer is typically a vinyl addition compound that incorporates a quaternary ammonium group and contains a $C_4$–$C_8$ alkyl, aryl, aralkyl or alkaryl pendant group. Typically this can be a $C_4$–$C_8$ halide quaternized dimethylamino ethyl(meth)acrylate. A preferred cationic monomer for this invention is benzyl chloride quaternized dimethylaminoethyl acrylate ("MADQUAT"). The presence of cationic monomer may also increase particle size in the product, in a direct relationship between amount of cationic monomer and average size.

The hydroxy polymeric polymerization stabilizer which eventually becomes incorporated onto the exterior of the organic polymer particles can be any polyhydroxy compound suitable as a polymerization stabilizer. Typically this can be a polyvinyl alcohol or a cellulosic ester. Polyvinyl alcohols are derived from the hydrolysis of polyvinyl acetate. Different grades of polyvinyl alcohol with different degrees of conversion can be formed depending on how much of the original hydrophobic character needs to be retained. For the purposes of this invention at least 80%, more preferably at least 90% of the vinyl acetate units should have been converted into vinyl alcohol units.

It may also be possible to impart some or all of the cationic functionality to the final polymeric particles by incorporating cationic monomer units into the polyhydroxy polymer. One example of this would be to first provide a copolymer of vinyl acetate with vinyl acetamide and then hydrolyze this to a polymer which would then have vinyl alcohol units and vinyl amine units. The vinyl amine units can be rendered cationic by subsequent protonation.

The particles themselves are insoluble in water, so that they can be deposited from an aqueous wash or rinse liquor.

The functional polymer at the exterior of these particles may form, or be included within a coating or incomplete coating on these individual particles. The hydroxy functional polymer is preferably nonionic or cationic. It will be explained below that it generally constitutes between 1 and 25% of the weight of the perfume-containing particles, usually between 1 and 10%.

Particle Size

Polymer particles of this invention desirably have an average particle size of at least 10 $\mu$m, better at least 20 $\mu$m or 30 $\mu$m, even better at least 40 $\mu$m, for ease of handling. The rate of release of any active ingredient in the particles may be faster than desired if the particles are of very small size such as average size of 1 $\mu$m. The polymer particles desirably have an average size not larger than 150 $\mu$m, better not over 125 $\mu$m so that the particles are not easily visible after deposition.

For particles intended to be used in fabric washing or conditioning, it is especially preferred to use particles with a mean size of at least 40 $\mu$m, e.g. 40 to 100 $\mu$m.

For particles intended for other products, e.g. personal washing products, a faster rate of release may be desired than with fabrics products, although retention and delay in release for some hours is still desirable, consequently a smaller particle size may be advantageous, such as a mean size in the range from 10 to 50 $\mu$m.

Polymerization techniques generally produce a range of particle sizes. For this invention it is desirable that a high proportion of the particles lie between the above limits on particle size. Thus, when particles are intended for fabric treatment, preferably 90% or more of the particles are larger than 30 $\mu$m. Preferably also 90% or more of the particles are not larger than 150 or even 125$\mu$. Better, 95% or more are not larger than 125 or even 100 $\mu$m. Preferably less than 4% of the water soluble organic polymer particles have a particle size of less than 10 microns. More preferably, less than 3% of the water-soluble organic polymer particles have a particle size of less than 10 microns.

To achieve these criteria, it may be necessary to sieve the particles and thereby separate oversized and/or undersized particles. An important aspect of reducing the amount of emulsion polymer formed (broadly speaking, polymer beads of a size below 10 $\mu$m) is to use an initiator system that is substantially insoluble in the aqueous phase, so as to prevent initiation of monomer molecules held in micelles. Suitable water insoluble initiators include azo compounds such as azobisisobutyronitrile (AIBN) and higher alkyl peroxides.

Hydroxy Functional Polymer

This polymer bearing hydroxy groups and located at the exterior of the particles serves to enhance deposition onto (or retention on) skin, hair, hard surfaces especially vitreous surfaces and fabric.

This polymer is desirably such that at least 80% of the monomer residues in the polymer contain at least one free hydroxy group able to participate in hydrogen bonding. The polymer is preferably nonionic and such that, in its pure state, it is water-soluble. However, when attached to the exterior of the particles, it does not render them water soluble. It is attached in such a way that it is not washed off completely upon contact with water. In some instances there may be chemical bonding, even in a form of grafting.

The preferred polymer is polyvinyl alcohol.

As is well known, polyvinyl alcohol cannot be prepared directly by polymerization, and is obtained by the hydrolysis of polyvinyl acetate. This hydrolysis generally stops before completion, and polymers with varying amounts of hydrolysis are commercially available.

We have found that deposition of particles, especially onto fabric, is better when the polyvinyl alcohol exhibits a substantial level of hydrolysis.

We may therefore prefer to use polyvinyl alcohol which is 85 to 100% hydrolyzed i.e. in which 85 or 88 to 100% of the acetate residues have been removed by hydrolysis. More preferably, the polyvinyl alcohol is at least 90% better at least 96% hydrolyzed, e.g. 96 to 99% hydrolyzed.

Another possible polymer is a copolymer of polyvinyl alcohol, available through hydrolysis of the corresponding copolymer of vinyl acetate. For example a copolymer of vinyl acetate and vinyl formamide, with a high proportion of vinyl acetate can by hydrolyzed to a copolymer of vinyl alcohol and vinyl formamide. Further hydrolysis of such a polymer converts the formamide residues to amine groups, giving a cationic copolymer of vinyl alcohol and vinyl amine.

Another category of polymers which can be used is cellulose and chemically modified cellulose where the modification does not greatly reduce the number of hydroxyl groups present. Examples of polymers in this category are hydroxyethyl cellulose, and hydroxypropyl cellulose.

Hydroxyethyl cellulose is available commercially and is made by treatment of cellulose with sodium hydroxide, followed by reaction with ethylene oxide. Another possibility is cellulose which has been chemically modified by the introduction of cationic substituent groups.

It is a characteristic of many grades of polyvinyl alcohol and of hydroxy ethyl cellulose that free hydroxy groups constitute more than 20%, often more than 25% of the weight of the polymer.

Solid Particles

For this invention it is preferred to use polymer particles which are solid—although they may be porous as well as solid—rather than particles in the form of hollow capsules.

Advantages of solid particles are that the desired size range is accessible, and that the polymerization reaction can be carried out in the absence of perfume.

The particles could possibly be porous particles made by polymerization around a liquid pore-forming agent, as taught in EP-A-285694. However, we have found it to be unnecessary to include such a pore-forming agent. Polymers formed by simple polymerization of a monomer mixture are able to absorb and carry active ingredients.

Preferred polymer particles may be formed by the polymerization of vinyl monomers, with some cross linking and/or chain branching agent included in the monomers which are polymerized, so that some cross links are formed between the polymer chains. If a cross linking agent is used, the proportion of cross linking may be low, so that after polymerization there may be some polymer chains which remain entirely linear and are not cross linked to any other chains.

A number of vinyl monomers containing a single carbon-carbon double bond may be used. One suitable category of monomers is the esters of acrylic and alkyl acrylic acids, of formula

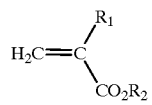

where $R_1$ is hydrogen or alkyl of 1 to 6 carbon atoms, preferably 1 to 3 carbon atoms and $R_2$ is alkyl (including branched and cycloalkyl) of 1 to 7 or 8 carbon atoms, preferably 3 or 4 carbon atoms in a straight or branched chain, or 7 carbon atoms in a bridged ring.

Specific examples of suitable monomers are isobutyl methacrylate (which is particularly preferred), n-butyl (meth)acrylate, isobutyl acrylate, n-propyl acrylate, isopropylmethacrylate and norbornyl (meth)acrylate. Less preferred is methyl methacrylate.

Another suitable monomer is styrene.

It is possible to use simple linear polymers. However, these can give particles which are somewhat sticky, and it is usually convenient to introduce some cross-linking or chain branching.

Cross linking between polymer chains formed from the above monomers can be achieved by including in the monomer mixture a small proportion of a monomer with two carbon-carbon double bonds, often termed polyolefinic or multifunctional cross-linking monomers. The use of such a material to provide cross linking is well known in other applications of polymers, although it is usual to introduce a greater proportion of cross linking than is required for this invention. Examples of this type of cross linking agent are divinyl benzene, diesters formed between acrylic acid and diols and higher ester formed between acrylic acid and polyols—which may be sugars.

Chain branching can be introduced by including among the monomers a hydroxyalkyl monomer of formula

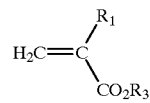

where $R_1$ is as specified above and $R_3$ is alkyl of 1 to 6 carbon atoms bearing at least one hydroxy group, preferably 3 to 4 carbon atoms in a straight or branched chain and bearing a single hydroxy group. These monomers undergo a side reaction during the course of polymerization, and this side reaction produces chain branching. When there is chain branching without cross linking, it is suitable that hydroxyalkyl monomer of the above formula provides from 10 to 40% by weight of the monomer mixture.

Suitable hydroxyalkyl acrylate monomers are hydroxypropyl methacrylate, hydroxybutylacrylate, and hydroxyethylacrylate.

Attachment of a polymer with hydroxy groups, notably polyvinyl alcohol, at the exterior of the particles, can be achieved by polymerizing the monomers in the presence of the polyvinyl alcohol (or other polymer with hydroxy groups) using the technique of suspension polymerization.

Suspension Polymerization

Suspension polymerization is a process in which the organic monomers are formed into a suspension in an aqueous phase, and polymerized. Polymerization of each suspended droplet leads to a bead of polymer.

During the polymerization process droplets of polymerizing monomer and polymer particles are constantly moving through the continuous suspension liquid and statistically there is a high probability of collisions between droplets and between particles. It is important that agglomeration of particles is prevented as this could very quickly result in loss of stability during the polymerization. It is customary to stabilize the suspension by incorporating a stabilizing agent in the aqueous phase before adding the monomer. Polyvinyl alcohol (PVA) is known to act as a stabilizer.

Polymerization may be carried out using a combination of PVA and second stabilizing agent which may or may not be a second hydroxy polymer. It is quite feasible to use a mixture of PVA grades. Examples of materials which can be used as second stabilization agents include other water soluble polymers such as polyacrylic acid or water soluble salts thereof. Typically the amount of stabilizer used is generally between 1 and 5% by weight of aqueous phase or 3 to 15% by weight of the monomer being polymerized, most preferably between 5 and 10% by weight of monomer.

It is possible to incorporate surfactants such as sodium oleate or sodium lauryl sulphate into the continuous aqueous phase to assist with the stabilization of the dispersed phase monomer droplets during the polymerization. Typically the surfactants used in this application are those which are preferentially soluble in the aqueous phase, typically surfactants which have an HLB of 8 or above. However, when choosing a surfactant in this invention it is important that it does not have an adverse effect on the droplet size and could result in the formation of unacceptably small sized polymer particles. It is particularly important to reduce the levels of emulsified droplets, which give rise to polymer particles below 10 microns. It is desirable to reduce the levels of emulsion to below 10%, particularly below 8%.

Thus, a typical polymerization procedure will commence by forming an aqueous solution of the hydroxy functional polymer which acts as stabilizing agent, together with a polymerization initiator, in a reaction vessel. Then while agitating the contents of the reaction vessel, the organic monomers are progressively fed in so that the monomers become dispersed in the aqueous phase and polymerize therein. The addition of monomers can be continued until the mixture in the reaction vessel is a slurry of polymer beads containing about 30% by weight of polymer.

In a possible variation of this procedure some of the monomer is dispersed in the aqueous solution of stabilizing agent before any polymerization initiator is added. In another possible variation the monomers are emulsified in water before they are added to the reaction vessel.

Suspension polymerization typically produces polymer beads with a diameter larger than $100\mu$. Smaller particle sizes in the range of $50-100\mu$ can be obtained by increasing the amount of stabilizer in the aqueous phase, or by increasing the amount of agitation, or both.

Further examples of materials which can serve as a second stabilizing agent include sodium oleate and sodium lauryl-sulphate, both of which are anionic surfactants, also nonionic surfactants with HLB of 8 and above, such as $C_{13}/C_{15}$ alcohol ethoxylated with 3 to 11 ethylene oxide residues, and sorbitan ester surfactants of similar HLB.

The amount of hydroxy functional polymer present in solution as a stabilizing agent will generally be between 1% and 5% by weight of the aqueous phase in which polymerization occurs. Larger amounts can also be used.

The amount may well be between 3% and 15% by weight of the monomers undergoing polymerization, possibly between 5% and 10%.

Observation by microscopy of such particles showed the hydroxy functional polymer to form a coating or incomplete coating of the particles, from which it can be estimated that the amount of hydroxy functional polymer attached to the particles was at least 1% by weight of these particles after (and also of course before) the incorporation of perfume.

Cross-linking

Cross-linking between polymer chains formed from the above monomers can be achieved by including in the monomer mixture a proportion of a monomer with two or more carbon to carbon double bonds, often termed polyolefinic or multifunctional cross-linking monomers. The use of such polyolefinic monomers to provide cross-linking is well known in the application of polymers. In generally, as the degree of cross-linking increases the ability for a polymer to swell in solvents decreases but the rigidity and glass temperature increases. In some applications such as synthetic rubber the rigidity and durability of the polymer are important characteristics and so the degree of cross-linking would be high.

The properties of the beads produced by suspension polymerization can be influenced by the degree of cross-linking. As mentioned previously a function of the polymerization stabilizer is to prevent the agglomeration of polymerizing particles. During the polymerization process the cross-linking monomer becomes incorporated causing cross-linking between polymer chains to form a three dimensional network. Cross-linking results in the surface properties of the polymerizing beads being much less sticky and much less prone to agglomeration when collisions occur.

In this invention it is important that the polymer can swell sufficiently in the liquid medium that comprises active material to allow said active material to penetrate the polymer particles but important that the polymer matrix retains its form and does not dissolve. The amount of cross-linking is much lower than say for synthetic rubber. Generally a suitable amount of cross-linking agent for this invention is not over 5 mole % of the monomer mixture and is preferably in the range from 0.5 to 3 mole %.

It is important that the polyolefinic monomer is soluble in or miscible with the hydrophobic monoolefinic monomer used and that the reactivity ratios are such that the polyolefinic monomer will readily copolymerize with the hydrophobic monoolefinic monomer. Examples of polyolefinic monomers used as cross-linking agents include divinyl benzene and diesters of acrylic acid or methacrylic acid with diols and diesters or higher esters formed between two or more moles of acrylic acid or methacrylic acid and polyols for example polyethylene glycol diacrylate.

Hydroxy substituted acrylate esters can also lead to cross-linking. The mechanism by which they do so is a side reaction which is not fully understood. When used, a suitable amount may lie in a range from 3 to 30 mole % of the monomer mixture. Preferably 10 to 30 mole %.

After the manufacture of the particles by polymerization, the direct product is in the form of an aqueous slurry. If desired, the particles may be separated from the aqueous phase by filtration or centrifuging, possibly followed by drying.

Another possible route for the production of polymer particles is emulsion polymerization to yield an aqueous emulsion of very small polymer particles (typically of sub-micron size) followed by a drying step to agglomerate these particles into larger particles with a size of at least $20\mu$.

Absorption of perfume by the particles can be brought about simply by bringing the perfume and the particles into contact, and allowing them to stand. This may be done by mixing perfume with the particles after they have been separated from the aqueous phase, or it may be done by mixing perfume into an aqueous slurry of the particles and allowing the mixture to equilibrate. It can be done by mixing the particles and perfume separately into an aqueous liquid product and allowing that mixture to equilibrate.

Encapsulated Particles

A further possibility is to encapsulate a "core" of polymer as described above, with aminoplast resin, while providing hydroxy-functional polymer at the exterior of the capsules, and absorb perfume within the core.

Several typical procedures are available to produce such encapsulated polymer. One procedure is to form polymer beads, for example of an acrylate polymer, as described earlier, and dispense this organic mixture in an aqueous solution containing the hydroxy functional polymer and urea-formaldehyde precondensate. The mixture is agitated to keep the organic mixture in suspension. While maintaining solution temperature between 20° C. and 90° C., acid is then added to catalyze polymerization of the dissolved urea-formaldehyde precondensate. If the solution is rapidly agitated during this polymerization step, shells of water-insoluble, urea-formaldehyde polymer form around and encapsulate the dispersed organic mixture and molecules of the hydroxy-group containing polymer are incorporated in and at the exterior of these shells. Melanine-formaldehyde precondensate can be used in place of urea-formaldehyde, and may be preferred.

Another procedure is to form encapsulated core polymer, in the absence of perfume, and subsequently allow perfume to diffuse through the shell, into the core polymer. We have found that absorption of perfume is possible through a thin shell, even though a thicker hollow shell is capable of retaining liquid perfume. Suitably the weight of polymer forming the shell is less than the weight of polymer forming the core, and the shell to core weight ratio may lie in a range from 1:3 to 1:20, better 1:5 to 1:20.

Hydroxy functional polymer will generally provide a substantial proportion of the shell, yet constitute from 1% to 25% of the capsules.

For this procedure it has been found preferable to encapsulate monomer within an aminoplast shell, then polymerize the monomer to form a (preferably solid) core of polymer within the shell. Less preferred is to partially polymerize the core before encapsulation.

It is also possible to encapsulate a mixture of liquid monomer and fragrance, then polymerize. However, this necessarily exposes perfume to the polymerization reaction, whereas absorption of perfume through the shell into a previously polymerized core does not.

When a product contains particles in which perfume is absorbed within polymer which is encapsulated by a thin shell, perfume can diffuse through the shell, and can be released without rupture of the shell, although the release and dispersion of perfume will be slower than for neat perfume. Thus, encapsulated polymer with absorbed perfume can provide deposition and retarded release of perfume similarly to the (preferred) arrangement when perfume is absorbed in polymer beads which have hydroxy functional polymer directly at their exterior.

Examples of preparation and use of the particles will now be given.

EXAMPLE 1

A 700 ml reaction flask equipped with motorised stirrer, reflux condenser, thermometer and inlet tube for delivery from a peristaltic pump was placed in a water bath at about 65° C.

An aqueous phase was prepared by mixing hydroxyethyl cellulose (5 parts) and deionized water (168 parts). The hydroxyethyl cellulose had a degree of substitution of 2 and was available from Hercules Chemical Corp as NATROSOL 250L. This phase was mixed until the hydroxyethyl cellulose dissolved and was then charged into the reaction flask. Stirring was applied to the reaction flask.

A monomer phase was prepared by mixing iso-butyl methacrylate (70 parts) with a cross linking co-monomer which was 1,6-hexanedioldiacrylate (1.8 parts).

2,2'-azo(bis)isobutyronitrile [usually abbreviated to AIBN] (2 parts) was added directly to the reaction flask and dispersed for about five minutes.

The monomer phase was added to the stirring reaction flask using a peristaltic pump over about ninety minutes. After addition the reaction mass was stirred at about 65° C. for about three hours and subsequently cooled.

The polymer beads were recovered from the aqueous slurry by filtration and air dried. The beads were sieved to separate the fraction with size below 125 µm.

It can be seen that in this Example, the total quantity of hydroxy-functional polymer was less than 10% by weight of monomers, and only part of that quantity becomes attached to the polymer beads.

The cross linking agent is 2% by weight and 1.63% by mole of the monomer mixture.

EXAMPLE 2

A 700 ml reaction flask, equipped as in Example 1, was placed in a water bath at about 65° C.

An aqueous phase was prepared by mixing poly(vinyl alcohol) available as Gohsenol AH-22 from Nippon Gohsei British Trades and Shippers Ltd, Dagenham, Essex and having a degree of hydrolysis of 97 to 98.8% (5 parts) and deionized water (168 parts). This phase was stirred until the poly(vinyl alcohol) dissolved and was then charged into the reaction flask. Stirring was applied to the reaction flask.

A monomer phase was prepared by mixing styrene (68 parts) and 1,6-hexanedioldiacrylate (1.8 parts).

AIBN (2 parts) was added directly to the reaction flask and dispersed for about five minutes.

The monomer phase was added to the stirring reaction flask using a peristaltic pump over about ninety minutes. After addition the reaction mass was stirred at about 65° C. for about three hours and subsequently cooled.

At this stage, the products was in the form of an aqueous slurry from which the polymer beads were recovered by filtration and air dried.

EXAMPLES 3 to 5

The procedure of Example 2 was repeated with different monomers as follows:

Example 3: Methyl methacrylate (70 parts) and 1,6-hexanedioldiacrylate (1.8 parts)

Example 4: n-Butylmethacrylate (70 parts) and 1,6-hexanedioldiacrylate (1.8 parts)

Example 5: iso-butylmethacrylate (54 parts) and hydroxypropylmethacrylate (18 parts)

In each of these examples the monomers were satisfactorily converted to polymer beads. These were recovered by filtration and air dried.

EXAMPLE 6

Beads, produced as in Example 5, were sieved to remove any beads larger than 75 µm diameter.

A perfume was prepared consisting of equal amounts of
i) dihydromyrcenol (2,6-dimethyl-7-octen-2-ol)
ii) anisaldehyde
iii) dimethylbenzylcarbinyl acetate
(iv) 1,1,2,4,4,7-hexamethyl-6-acetyl-1,2,3,4-tetrahydronaphthalene, available under the trademark "TONALID",
(v) 3a,4,5,6,7,7a-hexahydro-4,7-methano-1(3)H-inden-6-ylpropionate, available under the trademark "FLOROCYCLENE", Perfume-loaded polymer beads were prepared by mixing the above beads and perfume into a diluted rinse conditioner, to yield an aqueous slurry containing:

| | |
|---|---|
| Polymer beads | 10.71% |
| Perfume | 10.71% |
| Dihardened tallow dimethyl ammonium chloride | 3.5% |
| Water | Balance |

This slurry was agitated for two hours and left to stand for twenty four hours, after which it appeared that all the perfume had been absorbed into the polymer beads.

This slurry was added to a quantity of a rinse conditioner formulation which was an aqueous emulsion containing a 1,2-dihardened tallowloxy-3-trimethyl ammoniopropane chloride (HTTMAPC) as cationic softener. This material is disclosed in U.S. Pat. No. 4,137,180.

The formulation contained:

| | |
|---|---|
| HTTMAPC (including some fatty acid impurity) | 13.5 |
| Ethoxylated Coconut alcohol (20EO) | 0.75% |
| Hardened tallow alcohol | 0.75% |
| Calcium chloride | 0.2% |
| Preservative | 0.02% |
| Demineralized water | Balance to 100% |

After adding the slurry, the resulting perfumed formulation contained 0.75% by weight perfume, carried in polymer beads. The perfumed rinse conditioner formulation was agitated for two hours and then stored for six days in a closed container. A control formulation contained 0.75% by weight perfume, and the same concentration of fabric softener, without polymer beads.

To test perfume deposition, this rinse conditioner formulation and the control formulation were both diluted with water to provide rinse liquors containing 0.5% of the rinse conditioner formulation.

Test pieces of fabric were de-sized cotton terry towelling, approximate weight 25 g. For each test, a piece of terry towelling was weighed accurately and treated with 30 times its own weight of rinse liquor, in a Tergotometer pot, stirring at 80 rpm for 20 minutes. The cloth was then wrung out by hand, and line dried.

The amount of perfume in the fresh and used rinse liquors was determined by solvent extraction from 100 g of rinse liquor and gas chromatographic (GC) analysis of the solvent extract. The percentage deposition of perfume materials onto the cloth was calculated for three of the five materials. The results obtained were:

| | % Deposition | |
|---|---|---|
| Ingredient | Control | Perfume in polymer beads |
| Dihydromyrcenol | 14 | 25 |
| DMBCA | 24 | 33 |
| Florocyclene | 38 | 42 |

The amount of perfume on the dry cloth was determined by extraction of 5 g of dry cloth with 20 ml ethyl acetate, followed by GC analysis of the solvent extract.

The amount of perfume detected was expressed as a percentage of the theoretical maximum quantity (which would be present if there were complete deposition onto fabric and no subsequent losses).

The results obtained for materials were:

| | % Ingredient remaining on dry cloth | |
|---|---|---|
| Ingredient | Control | Perfume in polymer beads |
| Dihydromyrcenol | not detected | 1.3 |
| DMBCA | not detected | 8.0 |
| Florocyclene | not detected | 9.8 |
| Tonalid 2 | 30.2* | 51.1* |

*= result possibly affected by other GC peaks.

EXAMPLE 7

Perfume mixture was incorporated into polymer beads, as set out in the previous Example, but with two ratios of polymer to perfume. These were 1:1 polymer to perfume and 1:2 polymer to perfume.

The resulting perfumed beads were incorporated into rinse conditioner formulations as in the previous example so as to provide 0.75% by weight perfume in each formulation. A control formulation contained 0.75% by weight perfume, but no polymer. These were diluted to rinse liquors containing 0.5% by weight fabric conditioner, and used to treat terry towelling as in the previous Example.

The treated cloths were assessed by a panel of eight people.

Assessments were made on damp cloth directly after treatment, on dry cloth 24 hours after treatment and on dry cloth five days after treatment.

The assessments were:

| Assessment Stage | Control (no polymer) | 1:1 polymer to perfume | 1:2 polymer to perfume |
|---|---|---|---|
| Damp Cloth | Strongest | Weaker than control Equal to (1:2) | Weaker than control Equal to (1:1) |
| Dry Cloth (24 hours | Intense Tonalid odor | Florocyclene, Tonalid and anisaldehyde odors Stronger than (1:2) | Florocyclene, Tonalid and anisaldehyde odors Weaker than (1:1) |
| Dry Cloth (five days) | Tonalid odor | Florocyclene, Tonalid and anisaldehyde odors Weaker than (1:2) | Florocyclene, Tonalid and anisaldehyde odors Stronger than (1:1) |

EXAMPLE 8

Beads were produced as in Example 2. The monomer mixture was isobutyl methacrylate (70 parts) mixed with 1,6-hexanedioldiacrylate (1.8 parts). Preparations were carried out using various grades of polyvinyl alcohol and some other materials as the stabilizer. The grades of polyvinyl alcohol differed in the extent to which they had been hydrolyzed from polyvinyl acetate.

The materials used were:

| Stabilizer | Hydrolysis | Tradename |
|---|---|---|
| A polyvinyl alcohol | 98–99% | Gohsenol N-300 |
| B polyvinyl alcohol | 97–98.5% | Gohsenol A-300 |
| C polyvinyl alcohol | 87–89% | Gohsenol GH-23 |

-continued

| Stabilizer | Hydrolysis | Tradename |
|---|---|---|
| D polyvinyl alcohol | 78–80% | Gohsenol KH-17 |
| E polyvinyl alcohol jointly with a surface active acrylamide copolymer | 97–99% | Gohsenol AH-22 |
| F polyvinyl alcohol jointly with a 95:5 copolymer of acrylamide and behenyl (25 ethylene oxide) methacrylate | 97–99% | Gohsenol AH-22 |
| G hydroxyethyl-cellulose | | Natrosol 250L |
| H surface active acrylamide copolymer (comparative example) | | MER 10 |

In all cases the dried beads were mixed with their own weight of a single perfumery material, Florocyclene, also used in Example 6. After mixing they were left to equilibrate overnight, then a small quantity of finely divided silica (2% based on the total weight of perfume and polymer) was added as a surface improving flow aid.

The perfume-containing polymer beads were mixed into rinse conditioner (as used in Example 6) using a magnetic stirrer. In each case the amount of perfume carrying beads was 1.5% by weight of the rinse conditioner, so that the quantity of perfume was 0.75% by weight of the rinse conditioner formulation. A control formulation was prepared containing 0.75% Florocyclene without the polymer.

Deposition onto fabric was assessed using test cloths made of cotton terry towelling, acrylic fabric, and polyester. The fabric washing procedure was the same as set out in Example 6. After treatment of the fabric and drying, the intensity of Florocyclene on groups of the dried test cloths was assessed by a panel of five assessors who ranked the cloths in order of intensity of Florocyclene. The following results were obtained as unanimous views of the assessors:

| On cotton test pieces | B>A>C>Control |
| | C>D>Control |
| | E>F>Control |
| and | G>H>Control |
| on acrylic test pieces | A>B>C>Control |

On polyester test pieces A,B and C were all stronger than the control, but the assessors were not unanimous as to which of the three gave the highest perfume intensity.

These results demonstrate that the polymer particles A,B,C and D made using polyvinyl alcohol as stabiliser and hydroxy-functional monomer all gave an increase in the perceived intensity of perfume on fabric. So did polymer particles E and F made using polyvinyl alcohol in a mixture of stabilisers. The polymer particles G made using hydroxyethylcellulose as stabiliser and hydroxy-functional monomer also gave an increase in the perceived intensity of perfume on fabric and were superior to the particles H made using a different polymer as stabiliser.

EXAMPLE 7

942 parts of water, 1228 parts of a 10% solution of 88% converted polyvinyl alcohol, 4 parts benzyl chloride quaternised dimethylaminoethyl methacrylate (MADQUAT) and 6 parts Tegofoamex defoamer were charged to a round bottomed reactor vessel. The stirrer was started at 150 rpm and a nitrogen bleed was applied and the contents of the vessel were warmed to between 60 and 62° C. 12.3 parts of Vaso 67 thermal initiator slurried in 36 parts of water was then added to the contents of the vessel. A monomer blend comprising 1225 parts of isobutyl methacrylate and 24.5 parts butane diol diacrylate were then charged to the reactor over 1 hour to provide reaction solids of 35%. The temperature of the reaction needed was held at 60–62° C. until monomer addition was completed and then the temperature of the was allowed to rise under the reaction exotherm to 80° C. where it was held for 3 hours. The reaction medium was then cooled and the particle size range of the polymer was established as 40–900 microns with a means of 81.1 microns. The composition contained less than 9% emulsion, i.e. of beads less than 10 µm.

EXAMPLE 8

Example 7 was repeated but in a flat bottom vessel with a stirrer speed of 300 rpm and using lauryl peroxide as the initiator. The particle size range was from 20–200 microns, with a mean particle size of 79 microns. The composition contained less than 8% emulsion.

EXAMPLE 9

Example 7 was repeated by varying the amount of hydrophobic monomer blend charged to the reactor so as to provide reaction solids of 30%, 35% and 40%. The results are as follows:

| Solids | Particle Size Range of Beads | Emulsion |
|---|---|---|
| 30% | 40–350 microns | 27.7% |
| 40% | 10–200 microns | 24.6% |

EXAMPLE 10

Example 7 was repeated at 25% solids content but varying the amounts of stabilizer, defoamer and cationic monomer.

| % Stabilizer | Additions | Particle Size Range | Emulsion |
|---|---|---|---|
| 10% PVA | 2% Lauryl bromide quaternised dimethyl aminoethyl methacrylate dimethyl | V.thick bimodal 6–200 microns | not measured |
| 5% PVA | 2% Arquad T-30 | Small lumps aggregated beads | not measured |
| 5% PVA | 2% Disponil A3065 | V.Broad distribution | not measured |
| 10% PVA | 1% NaCl and 5% Methyl end capped PEG 2000 | 40–400 microns | 46.3% |
| 10% PVA | 1% NaCl 5% MPEG 1000 | Bimodal 40–400 microns | not measured |
| 10% PVA | 1% NaCl 10% MPEG 2000 | 40–150 microns | 36.8% |
| 10% PVA | 1% NaCl 5% Methyl end capped PEG 2000 2% Synperonic PE/L61 | 40–400 microns | 43.2% |

EXAMPLE 11

Example 7 was repeated using an amount of hydrophobic monomer that would provide a reaction medium of 25% solids and different grades of polyvinyl alcohol were used having different degrees of hydrolysis. In one test sodium chloride was added to the aqueous phase and the tests using 98% hydrolysed PVA, lauryl bromide quaternized dimethylaminoethyl methacrylate was used in place of the benzyl chloride quaternary cationic monomer.

| % Stabilizer | Stabilizer type | Additions | Results |
|---|---|---|---|
| 10% | 88% hydrolyzed (high mol wt) | | 100–200 microns |
| 10% | 73% hydrolyzed | | 100–200 microns |
| 10% | 88% hydrolyzed (high mol wt) | 1% NaCl | Large beads formed |
| 5% | 98% hydrolyzed | 0.15% Lauryl Bromide Quat | Polymer turned solid |
| 5% A-300 | 98% hydrolyzed | 0.2% Lauryl Bromide Quat | Large beads formed |
| 10% A-300 | 98% hydrolyzed | 0.5% Lauryl Bromide Quat | Very small beads formed |

EXAMPLE 12

Example 7 was repeated but using different levels of stabilizer.

| % Stabilizer | Results |
|---|---|
| 15% | 0.2–150 microns, mean 13 microns |
| 10% | 20–400 microns, mean 109 microns |
| 7.5% | 20–400 microns, mean 122 microns |
| 5% | 20–900 microns, mean 105 microns |
| 2.5% | 60–800 microns, mean 222 microns |

EXAMPLE 13

Example 7 was repeated using the following cationic monomers:

| Product | Cationic Monomer Used |
|---|---|
| A | teriary butyl aminoethylmethacrylate (TBAEMA) |
| B | Methyl chloride quaternized DMAEMA (MBJ) |
| C | Dimethyl aminopropyl methacrylamide (DMAPMA) |
| D | Benzyl chloride quaternized DMAEMA (MADQUAT BZ 75) |

In performance tests the products A–D were dispersed into a perfume base having a cationic character to assess whether the particles form agglomerates. Products A and B formed agglomerates, product C formed some agglomerates but D was almost free of agglomerates.

EXAMPLE 14

Example 7 was repeated using DMAPMA acetate salts, with different degrees of neutralization, as the cationic monomer component. The amount of emulsion produced was measured.

| Additions | Results | Emulsion |
|---|---|---|
| 2% DMAPMA 100% neutralised | pH 5.42 | 33% |
| 2% DMAPMA 75% neutralised | pH 8.0 | 28.7% |
| 2% DMAPMA 50% neutralised | pH 8.4 | 18.9% |
| 2% DMAPMA 25% neutralised | pH 8.6 | 19.6% |

EXAMPLE 15

Example 7 was repeated but using various levels of benzyl chloride quaternised dimethylaminoethyl methacrylate.

| Amount of cationic monomer | Performance test in perfume base | Emulsion |
|---|---|---|
| 1.0% | no agglomerates occurred | 16.2% |
| 0.5% | no agglomerates occurred | 13.0% |
| 0.2% | virtually none | 17.9% |
| 0.1% | formed small white agglomerates | 15.8% |

EXAMPLE 16

The polymer particles produced in Example 7 evaluated by assessing the ability to absorb water insoluble active ingredients. 10 parts of beads were dispersed into 10 parts of liquid water insoluble active ingredients and the quantity of liquid absorbed was observed visually.

| Active | Description | Volume pre Absorption | % Absorption |
|---|---|---|---|
| Propischlor | Herbicide | 1 | 0 |
| Gossyplure | Semio Chemical | 1.2 | 100 |
| Methyl Eugenol | Semio Chemical | 1 | 100 |
| Trimedlure | Semio Chemical | 1 | 50 |
| Spiroketal | Semio Chemical | 1 | 100 |
| Pyrethrum Extract 25% Active in parraffinic solvent | Insecticide | 1 | 20 |
| Pyrethrum Extract 50% Active | Insecticide | 1.1 | 50 |
| Ethion | Insecticide | 1 | 50 |
| Cypermethrin 50% Active in Solvesso 200 solvent | Insecticide | 2 | 50 |
| Furfural | Soil Sterilant | 1 | 100 |

EXAMPLE 17

A preparation of isobutyl methacrylate polymer was repeated with differing quantities of MADQUAT as the only variable. The results show that mean particle size increases with quantity of such a cationic monomer.

| % MADQUAT | Mean particle size, $\mu m$ |
|---|---|
| 0.22 | 74 |
| 0.3 | 98 |

-continued

| % MADQUAT | Mean particle size, μm |
|---|---|
| 0.4 | 109 |
| 0.5 | 165 |

What is claimed is:

1. Water-insoluble organic polymer particles formed of hydrophobic core polymer and having at their surface at least one further free-hydroxy-containing polymer which contribute(s) a hydroxyl and a cationic functionality at that surface, wherein the cationic functionality is provided by pendant cationic groups that have been derived from cationic vinyl addition monomer units which are either bonded to the organic water-insoluble polymer or are cationic monomer units present in the further free-hydroxy-containing polymer.

2. Polymeric particles according to claim 1 wherein the particles have an average particle size of at least 40 microns but no more than 150 microns.

3. Polymeric particles according to claim 1 wherein cationic functionality at the surface is provided by one or more cationic vinyl addition monomers selected from quaternized salts of dimethyl amino propyl acrylamide and dimethyl amino propyl methacrylamide.

4. Polymeric particles according to claim 1 wherein cationic functionality at the surface is provided by one or more cationic vinyl addition monomers selected from $C_4$–$C_8$ alkyl, aryl, alkaryl, and aralkyl halide of dimethyl amino (meth)acrylates.

5. Polymeric particles according to claim 1 wherein cationic functionality at the surface is provided by a benzyl-chloride-quaternized dimethyl amino ethyl methacrylate monomer.

6. Polymeric particles according to claim 1 wherein the core polymer is based on alkyl esters of acrylic acid or methacrylic acid.

7. Polymeric particles according to claim 1 wherein the core polymer is based on alkyl ester of acrylic acid or methacrylic acid and a multifunctional cross-linking monomer.

8. Polymeric particles according to claim 1 wherein the core polymer is based on isobutyl methacrylate and divinyl benzene.

9. Polymeric particles according to claim 1 wherein the further polymer providing hydroxy functionality is selected from polymers comprising vinyl alcohol units.

10. Polymeric particles according to claim 1 wherein the polymer providing hydroxy functionality is selected from polyvinyl alcohol comprising at least 80% vinyl alcohol units.

11. Polymeric particles according to claim 1 wherein the polymer providing hydroxy functionality is selected from polyvinyl alcohol comprising at least 85% vinyl alcohol units.

12. Polymeric particles according to claim 1 further comprising an active ingredient to be released in a controlled manner, wherein the active ingredient is selected from insecticides, curing agents and sunscreen agents.

13. Polymeric particles according to claim 1 which form stable dispersions in liquid medium containing active ingredients and remain substantially free from agglomerated particles.

14. Polymeric particles according to claim 13 which are capable of imbibing and entrapping the active ingredient, while remaining in suspension and substantially free from agglomerated particles.

15. A method of preparing polymeric particles according to claim 1 by suspension polymerization of hydrophobic monomers or monomer blend in an aqueous medium comprising a vinyl addition cationic monomer and as a polymerization stabilizer a polymer comprising free hydroxy groups.

16. A method of preparing polymer particles according to claim 1 by suspension polymerization of a blend of isobutylmethacrylate and dimethyl benzene in an aqueous medium comprising benzyl chloride quaternized dimethyl amino ethyl acrylate and as a polymerization stabilizer a polyvinyl alcohol.

17. A method of preparing polymer particles according to claim 15 or claim 16 wherein the suspension polymerization process is effected by azo or peroxide initiators.

18. A method of preparing polymer particles according to claim 1 wherein the cationic vinyl addition polymer is a benzyl chloride quaternized dimethyl amino ethyl (meth) acrylate and the resulting polymer particles which have an average particle size in the range 10 microns to 150 microns.

19. A method of preparing polymer particles according to claim 1 wherein less than 4% of the water-soluble organic polymer particles are of particle size less than 10 microns.

20. A method of preparing polymer particles according to claim 1 wherein less than 3% of the water-soluble organic polymer particles are of particle size less than 10 microns.

* * * * *